(12) United States Patent
Bertoli et al.

(10) Patent No.: US 10,405,969 B2
(45) Date of Patent: Sep. 10, 2019

(54) MEDICAL DEVICE FOR BREAST RECONSTRUCTION

(71) Applicant: Decomed SRL, Mogliano Veneto (TV) (IT)

(72) Inventors: Giovanni Bertoli, Mogliano Veneto (IT); Giorgio Berna, Treviso (IT); Guido Papaccio, Mestra (IT)

(73) Assignee: DECOMED SRL, Mogliano Veneto (IT)

(*) Notice: Subject to any disclaimer, the term of this patent is extended or adjusted under 35 U.S.C. 154(b) by 0 days.

(21) Appl. No.: 14/392,037

(22) PCT Filed: Sep. 16, 2013

(86) PCT No.: PCT/IT2013/000248
§ 371 (c)(1),
(2) Date: Mar. 9, 2015

(87) PCT Pub. No.: WO2014/041577
PCT Pub. Date: Mar. 20, 2014

(65) Prior Publication Data
US 2016/0250016 A1     Sep. 1, 2016

(30) Foreign Application Priority Data

Sep. 17, 2012  (IT) ............................ TV20120038 U

(51) Int. Cl.
*A61F 2/12* (2006.01)
*A61F 2/00* (2006.01)

(52) U.S. Cl.
CPC .............. *A61F 2/12* (2013.01); *A61F 2/0063* (2013.01); *A61F 2002/0068* (2013.01)

(58) Field of Classification Search
CPC ........................................................ A61F 2/12
(Continued)

(56) References Cited

U.S. PATENT DOCUMENTS 4,840,629 A * 6/1989 Bustos ....................... A61F 2/12
128/898
7,476,249 B2 * 1/2009 Frank ........................ A61F 2/12
623/8

(Continued)

FOREIGN PATENT DOCUMENTS

EP    2 524 670 A1    11/2012
FR       2746298 A1 *  9/1997  .......... A61F 2/0059
WO    2012/122215 A2   9/2012

OTHER PUBLICATIONS

Feb. 12, 2014 International Search Report issued in International Patent Application No. PCT/IT2013/000248.

*Primary Examiner* — Suzette J Gherbi
(74) *Attorney, Agent, or Firm* — Oliff PLC

(57) ABSTRACT

Medical device made of biomaterial, for implant-based breast reconstruction, having a flat original shape of plane geometry, with sections, which sutured together define the front part, lateral, upper and lower of a box element, at least one of the aforesaid sections having at least one appendix adapted to define the rear part of the box element, said box element being adapted to wrap and contain integrally a breast prosthesis, said box element being configured to be interposed between the subcutaneous layer and the pectoralis major muscle and being suturable to the latter.

10 Claims, 4 Drawing Sheets

(58) Field of Classification Search
USPC .......................................................... 623/7–8
See application file for complete search history.

(56) References Cited

U.S. PATENT DOCUMENTS

| | | | | |
|---|---|---|---|---|
| 7,819,918 | B2 * | 10/2010 | Malaviya | A61B 17/064 |
| | | | | 623/14.12 |
| 8,858,629 | B2 * | 10/2014 | Moses | A61F 2/12 |
| | | | | 623/8 |
| 9,277,986 | B2 * | 3/2016 | Moses | A61F 2/12 |
| 2002/0042658 | A1 * | 4/2002 | Tyagi | A61F 2/0063 |
| | | | | 623/23.72 |
| 2003/0212462 | A1 * | 11/2003 | Gryska | A61F 2/0063 |
| | | | | 623/23.72 |
| 2007/0088434 | A1 | 4/2007 | Frank | |
| 2012/0053690 | A1 * | 3/2012 | Frank | A61F 2/12 |
| | | | | 623/8 |
| 2013/0253645 | A1 * | 9/2013 | Kerr | A61F 2/12 |
| | | | | 623/8 |
| 2014/0257482 | A1 * | 9/2014 | Ward | A61F 2/0059 |
| | | | | 623/8 |
| 2015/0250582 | A1 * | 9/2015 | Greenhalgh | A61F 2/12 |
| | | | | 623/8 |

* cited by examiner

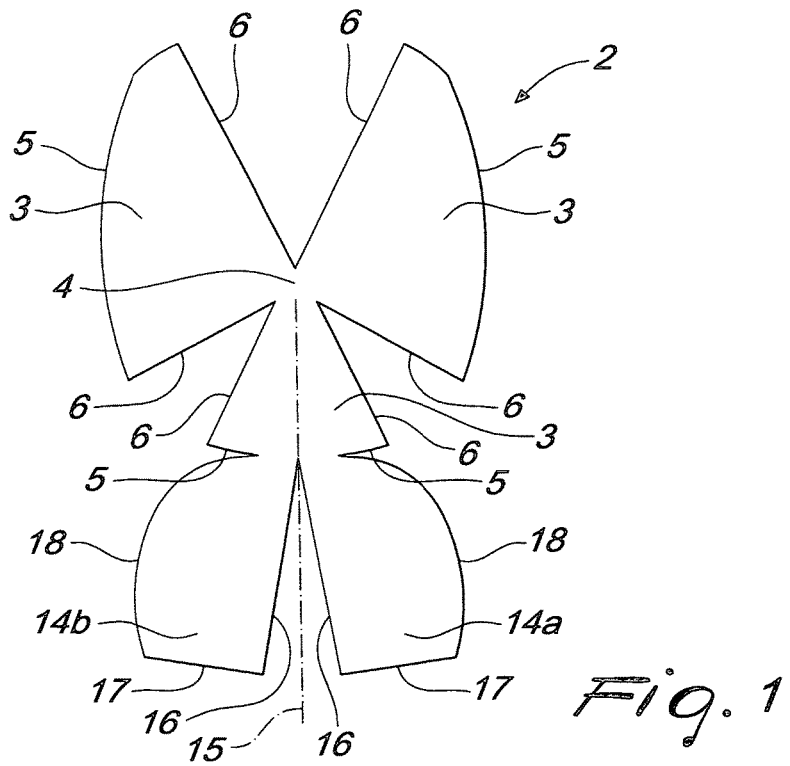
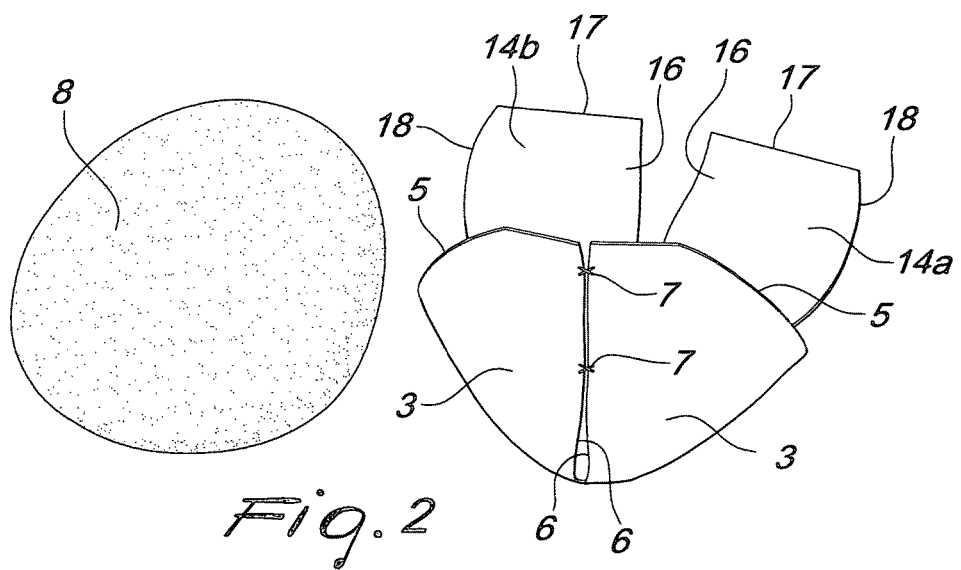

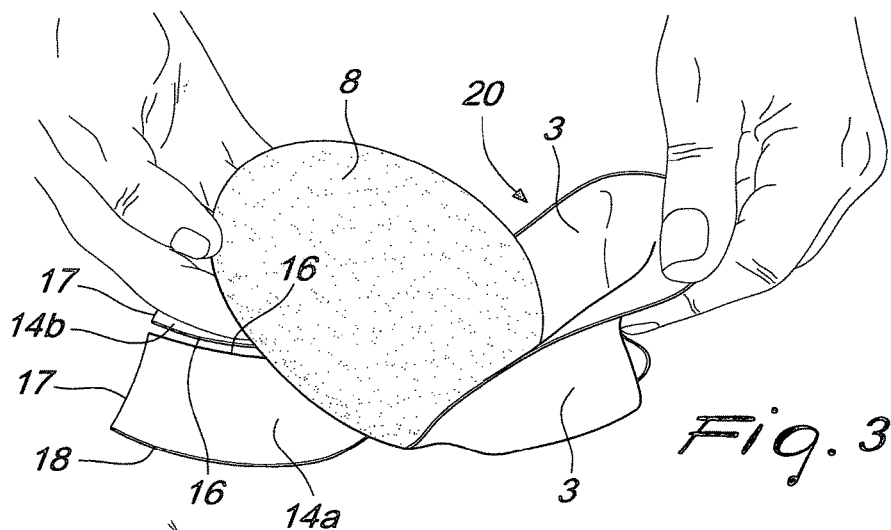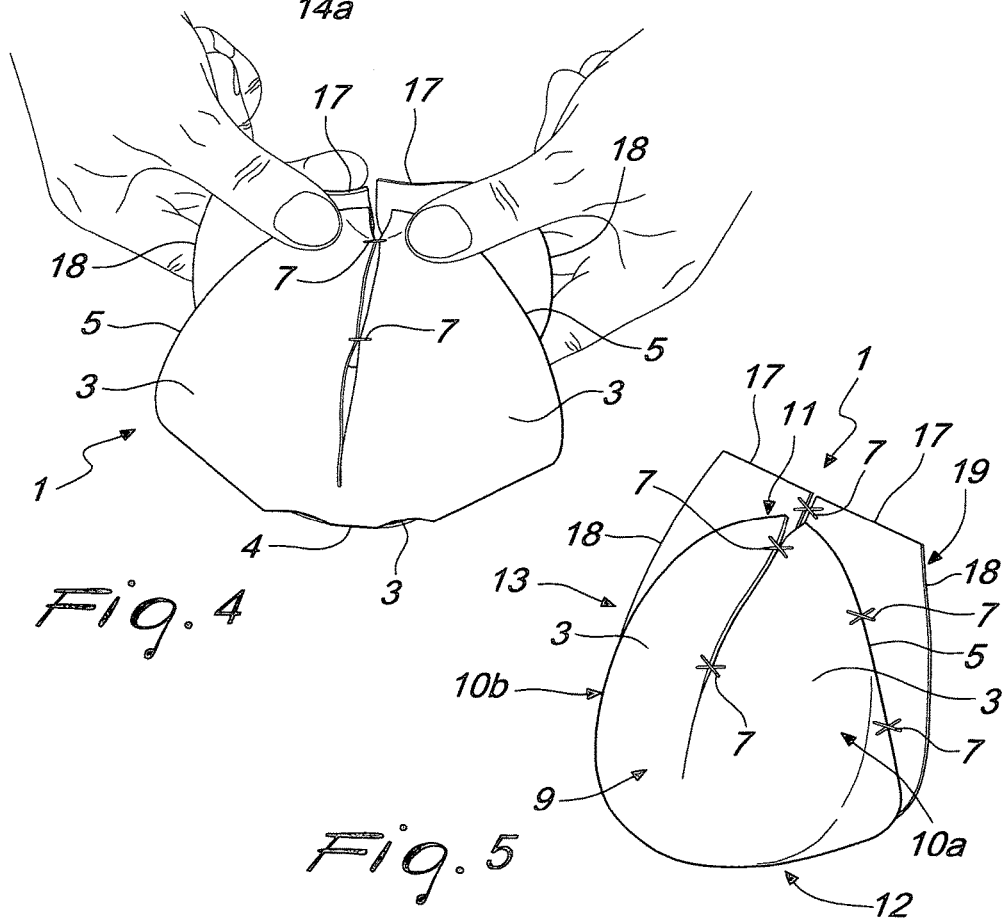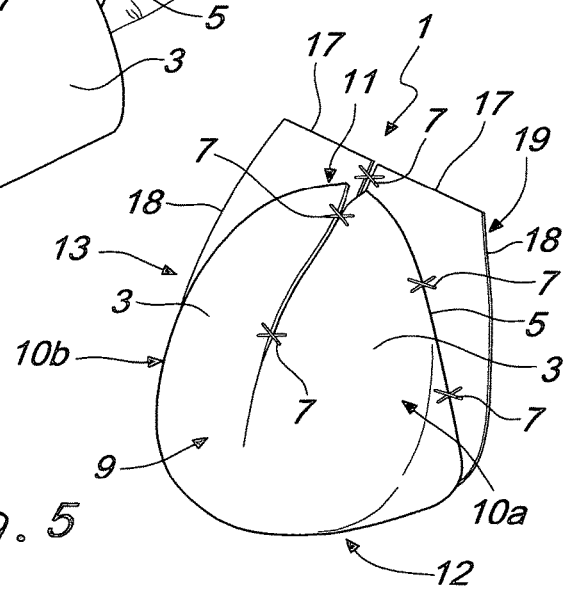

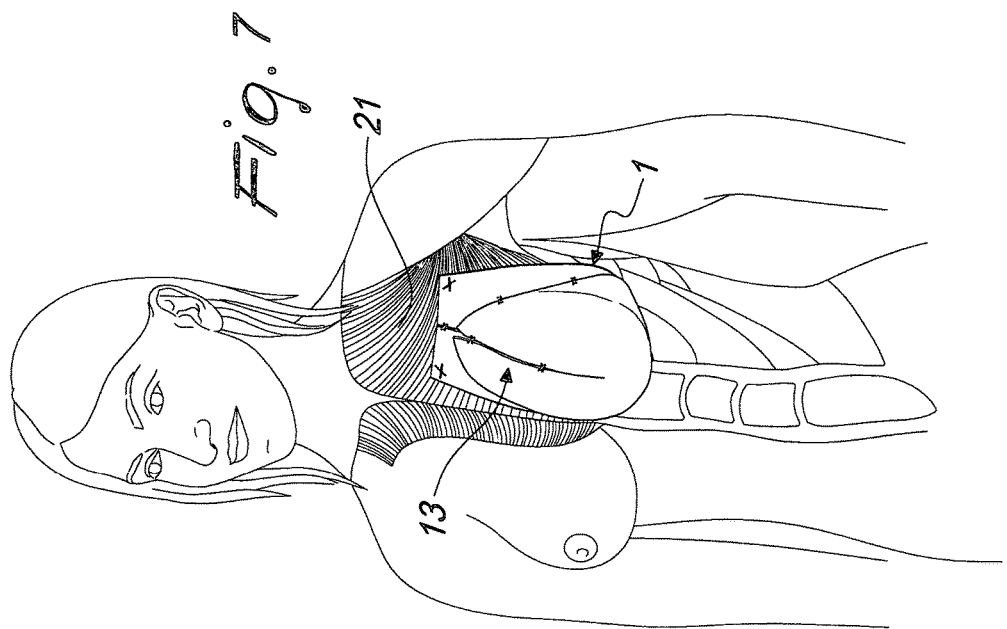
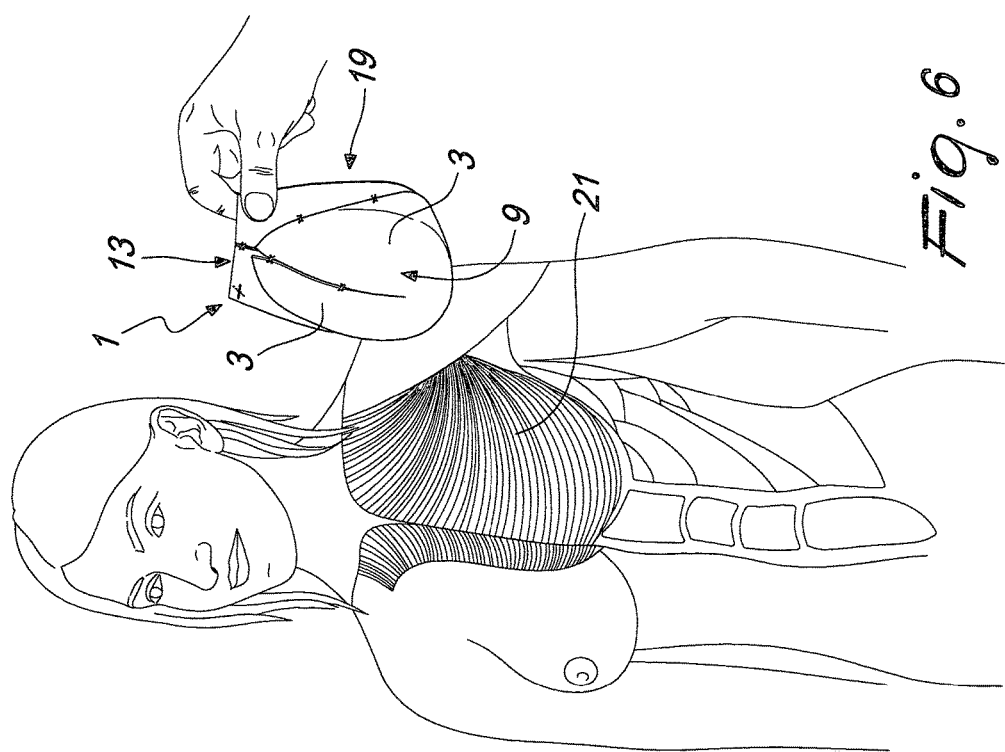

MEDICAL DEVICE FOR BREAST RECONSTRUCTION

1. FIELD OF INVENTION

The present invention relates to a medical device, specifically for breast reconstruction, after mastectomy.

2. BACKGROUND ART

Nowadays the necessity for providing a breast reconstruction after mastectomy is accepted.

The current surgery for breast reconstruction after mastectomy is divided into two techniques: one in two stages and one in a single stage.

For the two stage technique mastectomy, the surgeon prepares a submuscular pocket creating a space between the chest wall and the pectoralis major muscle, which is low-cut and etched down to the superficial fascia at its lower pole and medial to the fourth space intercostal.

It then proceeds laterally along the serratus muscle fascia.

An appropriate tissue expander is then placed inside and closes the pocket in such a way as to contain the whole device inside.

In the following days there is progressive inflation until the desired expansion has been achieved.

The expander is then removed no earlier than 4/6 months during a second operation that will include the removal of the expander and placement of the final prosthesis.

The single stage reconstruction technique involves the placement, after mastectomy, of a breast implant in a submuscular pocket, created with the technique described previously.

The breast implant is subsequently inserted into the submuscular cavity and is covered at its lower pole with a network of biomaterial thereby avoiding the need for muscle expansion.

The results of the two techniques are used for breasts of small and medium dimensions.

Large breasts currently represent an indication for reconstruction in two stages.

The results of the two techniques are similar from a physiological point of view, since, in any case, there is the dissection and resection of the pectoralis major muscle that entails its dislocation and therefore a substantial loss of movement.

With regard to the physiology of the pectoralis major muscle it can be stated that in case of disconnection, the movements that may be deficient are the anteposition and the arm flexion, internal rotation and adduction.

Moreover, considering the movement of the shoulder and upper limb, we must consider the synergistic action of various finely modulated muscle groups; also a modest quantity of weakening of these can alter the pace shoulder joint with an impact on the normal activities of daily life.

In fact, the pectoralis major muscle is located in the chest, anteriorly, between the medial part of the clavicle, sternum and cartilage of the first 6/7 coastline, the external aponeurosis dell'obliguo (medially) and the ridge under Annex E, Table I.

The muscle is divided into two parts: the head and the sternocostal head clavicular, which differ in their effects on the motility of the shoulder and upper limb.

The clavicular head flexes the arm and moves it forwards toward the contralateral shoulder and rotates it internally.

The sternocostal head depresses the shoulder, adducts the arm toward the contralateral iliac crest and rotates it internally.

The actions of this muscle can combine differently, between them and with the movements generated by many other muscles acting on the shoulder, allow normal movement.

The shoulder, both anatomical and functional, is an extremely complex mechanism that has a very large motor ability.

This entails the need to dispose of synergies of activation, regulation and balance of the various muscle components in relation to the control of the multiple parameters (direction, distance, strength, speed, endurance) to produce a movement qualitatively "normal", that is precise, smooth and suitable for the motor task required.

The movements which may be deficit, in the case of partial lesion of the pectoralis major, are the anteposition and the arm flexion, internal rotation and adduction, in a manner which is evident to a greater or lesser degree, in relation to the position and to the extent of the lesion.

In addition, with regard to the range of movement of the shoulder and upper limb, we must consider the synergistic action of various finely modulated muscle groups, the weakening of also a modest amount of which can alter the pace shoulder joint with repercussions on everyday life.

The state of the art is a prosthesis to maintain the position and shape of an organ (patent No. 2746298). The advantages of this new medical device when compared to the one above described are several:

a) the U.S. Pat. No. 2,746,298 can be used only over the organ of the breast still present in the human body, but cannot be used on a prosthesis when it is inserted after the removal of the mammary gland, following breast cancer or preventive treatment for breast cancer rather the invention is used to cocoon the breast implant when placing it over the pectoralis major muscle, once the mammary gland is removed.

b) the U.S. Pat. No. 2,746,298 is formed from two pieces which don't completely envelop the organ (breast), but it is only rested against it, with the only function being to "pull up" the breast (breast lift). The invention instead envelops an entire prosthesis and allows it to be attached over and in contact with the pectoralis major muscle during breast reconstruction after removal of the mammary gland.

c) the U.S. Pat. No. 2,746,298 is fixed on both sides (above and below): above (collarbone) and below (to the chest wall) precisely in order to maintain the new positioning of the breast in a fixed position. The invention instead is fixed exclusively on the pectoralis major muscle, leaving the lower pole free which allows the placement of the implant not to be fixed.

d) the function of the U.S. Pat. No. 274,698 is to replace a breast affected by ptosis in the position that it had been before the ptosis. It's a kind of internal bra that allows the organ which is still intact, healthy and not affected by cancer to be pulled up. The new feature of the invention is to completely wrap a breast prosthesis, not a gland, after the removal of the mammary gland, allowing the subcutaneous application in the cavity produced by the removal, rather than under the muscle.

Another patent (PCT/US2012/027975) speaks about systems and methods for mastopexy.

Patent n. US 2002/0042658 has a form and a function which is completely different.

a) Geometrically, in fact the diversity of forms emerges; the invention serves to wrap a prosthesis, while the cited patent (US 2002/0042658) serves to cover a defect in the abdominal wall.

b) the patent US 2002/0042658 has a central portion which is reinforced precisely in order to withstand the tension of the abdominal wall; the invention does not have portions reinforced due to not having to bear pressure having as a purpose to wrapping of a breast prosthesis.

c) the cited patent US 2002/0042658 is folded to be inserted within a tube inside the human abdomen and then re-opened to cover the defect of the abdominal wall. The invention, instead wraps a breast prosthesis and is then inserted already formed three-dimensionally inside the body.

d) the cited patent US 2002/0042658 has hooks for anchoring to the abdomen. The invention has no hooks, being only sutured to the pectoralis major muscle.

In the state of art there is also another patent (n. WO 2012/122215).

Patent no. WO 2012/122215 is a different device that does not solve many problems that, instead, the invention overcomes:

a) the form of the patent n. WO 2012/122215 has a main body with the strap. The shape and size "is sized to span substantially a portion of the lower pole of the breast and not cover the nipple areolar complex" (0023). The invention rather is an irregular shape devoid of the strap with a size and shape adapted to cover the entire prosthesis.

b) the patent n. WO 2012/122215 relates to a device that is a support in the lower pole breast integrates, in order to pull it out. The invention, however presupposes the removal of the mammary gland and the total coverage of the prosthesis, which is then inserted into the cavity created by the removal of the gland with the tumor. The invention then, does not include any anchor in the lower pole, which, other than as described in patent no. WO 2012/122215, leaves the lower pole free, being the invention sutured only to the pectoralis major muscle.

c) The patent no. WO 2012/122215 performs the function of lift up the breast to solve or prevent a ptosis. The invention instead performs the function of allowing the operating technique "muscle sparing", allowing the insertion of the prosthesis over the pectoralis major muscle.

Another patent is regarding three dimensional hernia mesh (EP 2524670A1).

To clarify the obvious differences, they are detailed below.

a) FIG. 17 of the patent EP 2524670A1 illustrates the folding plan for the implant. While the implant is folded into a three dimensional structure, it is folded into a vertical alignment made up of at least two layers superimposed by glueing or heat setting and wing bars. The structure of the patent n. EP 2524670A1 is a T profile or H profile while the invention has no layers, it envelops a breast prosthesis and sutured around a prosthesis without the use of thermofixing and/or glueing and has no wing bars.

b) The patent EP 2524670A1 is used for closing wounds and sealing defects in the inner and outer abdominal wall and strengthening it. The invention however is used to completely wrap a breast prosthesis during reconstruction after the removal of the mammary gland and is attached to the pectoralis major muscle.

c) Patent EP 2524670A1 is designed to be flexible so that turning is easily possible. It is characterized by outer edge which is upturned and can be fixed by glueing or heat setting or closed with a silicon layer. The invention is inserted preprepared and fixed into position. It is not flexible, does not have an outer edge and no silicone is used.

3. DETAILED DESCRIPTION

The main function of what forms the subject of this invention is therefore to solve the above mentioned technical problems, eliminating the drawbacks of the above mentioned prior to and thus providing an invention which allows the reconstruction of the breast, post-mastectomy, without compromising the functionality of the muscle.

Within the above aim, another important objective of the invention is to prevent any muscle damage between the medial part of the clavicle, sternum, cartilage of the first six/seven ribs, the external oblique aponeurosis (medially) and the ridge below the greater tuberosity of the humerus (laterally).

Another objective of the invention is to allow the maintenance of the movement of the pectoralis major muscle.

A further objective is to obtain an invention that, following mastectomy and breast reconstruction, avoids the need of rehabilitative therapies resulting in .sub.the elimination of the costs associated with these disabilities.

Another purpose is to produce an invention that produces a drastic reduction in postoperative pain.

An important objective is to obtain an invention that is effective, structurally simple, which presents realizable costs, that is realizable with the usual known systems and which is implantable without requiring special surgical techniques.

This aim and these objectives, and others which will become apparent hereinafter, are achieved from a medical device, specifically for breast reconstruction, which is characterized by the fact of being made up of a box element obtained from a flat sheet, realized in biomaterial, divided into multiple partitions, sewn together to define the parts of front, side, top and bottom of said box element, at least one of said partitions having at least one appendix adapted to define the rear of said box element, said box element being adapted to contain or containing integral breast implant, the said box element being inserted between the skin and the pectoralis major muscle and being suturabile to the same.

Further characteristics and advantages of the invention will become apparent from the detailed description of a specific, but not exclusive, embodiment, illustrated only by way of a non-limitative example in the accompanying drawings, in which:

FIG. 1 shows the device in the arrangement in plan;

FIG. 2 shows the device partially assembled to assume a conformed box;

FIG. 3 illustrates the positioning of the device within a breast implant;

FIG. 4 illustrates APPLIANCE assembled to make up the correct form for the breast implant;

FIG. 5 shows the device referred to in the previous figure in a three-quarter view perspective;

FIG. 6 shows the device before it is placed in between the skin and the pectoralis major muscle;

FIG. 7 shows the device sutured to the pectoralis major muscle; and

Figure 8:
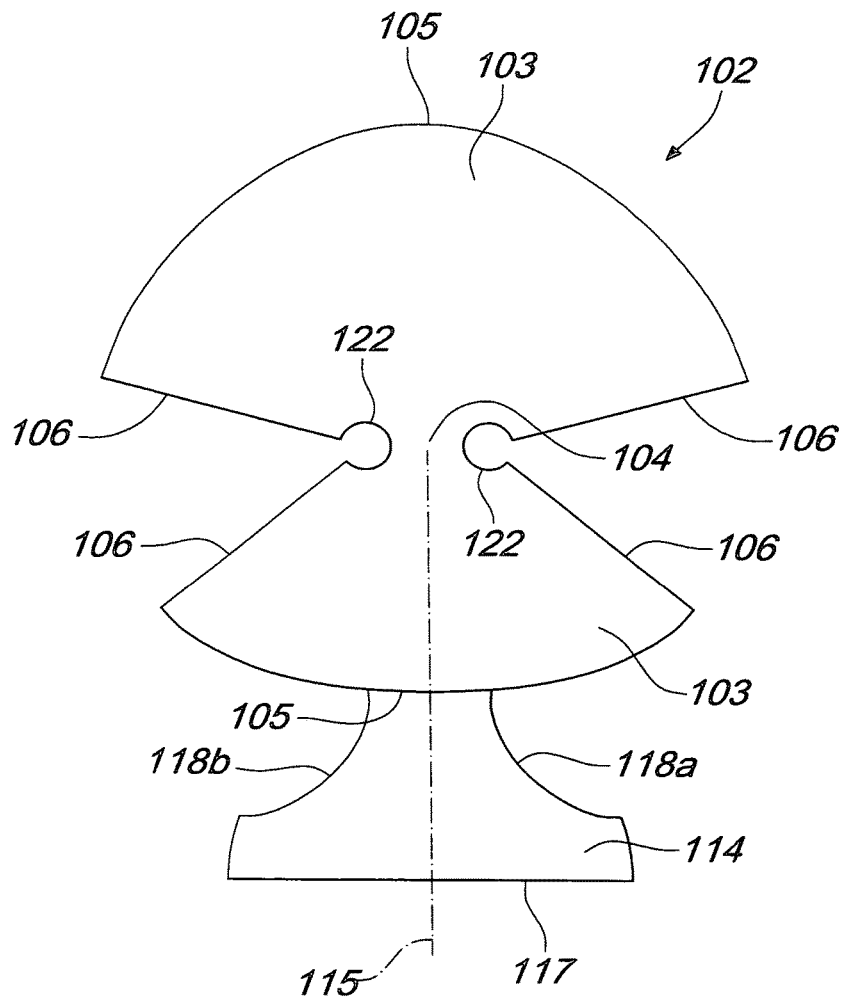
FIG. 8 illustrates a different form that the device assumes in the arrangement in plan.

In the realisations that follow, individual characteristics, given in relation to specific examples, may actually be interchanged with others (different characteristics that exist in other examples of realization).

Also note that if during the procedure of registration a patent is found to have already in place any part of the device to which this patent refers, then this claim should be considered with disclaimer to previously patented claims.

With reference to the above figures, a medical device is indicated with the number (1), that is used in breast reconstruction and which is constituted by a box element obtained from a flat sheet (2), made with a biomaterial, divided in two or more sections (3).

In the particular realisation illustrated in FIG. 1, the device (1) the plane sheet (2) is cut in order to define three distinct sectors (3) each of which comprises a substantially triangular shape with concentric vertices, which thus define a central zone (4) flat it can possibly be drilled, and first bases (5) are slightly arched.

The sections (3), are obtained in such a way that they can be folded by combining the respective first sides (6) and adjoining so that, once joined together by such sutures (7), define a containment structure (20) for a breast implant (8).

The sections (3), once pushed together and sewn at the respective first sides (6) define adjacent the front end (9), lateral (10a, 10b), upper (11) and lower (12) of a box element (13).

At least one of the two sections (3), and specifically the lower one of which a particular realization is illustrated in FIG. 1, presents two appendages (14a, 14b) projecting from the base (5), substantially equal to each other and are arranged approximately symmetrically to a longitudinal central axis (15) of the above section (3).

Each of the said appendages (14a, 14b) has a substantially triangular shape with a linear second side (16) and a third substantially arched side (18).

Once the breast prosthesis (inserted 8) corresponds with the structure of containment (20) obtained by sewing the sections (3) and then the second sides (16), adjacent to them, are sewn together by with one or more points of suture as seen in the illustrations (7) are sewn as well as the first bases (5) with the appendages (14a, 14b), as shown in FIG. 5.

The appendices (14a, 14b) are such as to define the rear part (19) of said box element (13) so that it completely encloses the breast prosthesis (8).

The said box element (13) is then interposed between the skin and the pectoralis major muscle (21) and is then suturable to the latter, as shown in FIGS. 6 and 7.

The flat sheet (2) is made of biomaterial, such as for example, the one known by the trademark "VYPRO" of the company Ethicon Products, or with the trademark "VYCRILL" distributed by the company Johnson & Johnson, or a polypropylene coupled to "Vycrill", or obtained through the use of suture thread of vegetable origin (such as flax or cotton) or synthetic (such as polyamides, polyester, polypropylene) or of mineral origin (steel), or biomaterial such as a synthetic mesh or network of the type known the brand "Tiloop BRA."

Said flat sheet (2) in fact constitutes a scaffold for the fixing to the pectoralis major muscle (21) of the box (13) and is adapted to ensure the continuing stability over time of the anatomical shape even when subjected to the force of gravity.

In practice it has been observed that the invention has achieved the intended aim and purposes mentioned above. Having obtained a medical device in the application of which does not compromise the functionality of the pectoralis major muscle, preventing any muscle damage between the medial part of the clavicle, the sternum, cartilage of the first six/seven ribs, the external oblique aponeurosis (medially), and the ridge below the greater tuberosity of the humerus (laterally).

The said device allows the maintenance of the movement of the pectoralis major muscle, avoiding the need for rehabilitation therapies, thus eliminating the costs associated with this disability.

The device also allows the achievement of a drastic reduction in postoperative pain, eliminates the risk of the muscle contracture; the muscle allows the maintenance of the stock in case of revision, requires less surgical time and reduced complexity of the operation given that the lack of dislocation of the prosthetic material is dynamic and static, and also of a reduction in bleeding.

Therefore a superior aesthetic result in both the short and long term.

In essence, the device is advantageous for the patient from various points of view, given that psychologically the patient is less affected given the rapidity of the intervention that can take place at a single time and with a simplified technique that, by eliminating the procedure of loosening the muscle, may take place more quickly, with less bleeding and decrease of blood loss and serous, with a lower risk during and after surgery; also physiologically the patient will not suffer any loss of movement due to resection/disconnection of the pectoral muscles and not clinically suffer pain to the same intensity and extent of previous surgical techniques and the recovery time will be significantly reduced, reducing the effect of the work life of the patient due to a more rapid reintegration into the workplace.

It will be possible to perform the same physical activities which are not recommended in the absence of said device and maintaining a high quality of life in normal daily tasks.

Anatomically, the pectoralis major muscle remains intact and its complete structure will not be affected and will eventually be available for a subsequent surgical operation that may involve muscle fascia.

The materials used and the dimensions that constitute the individual components of the invention may be more pertinent according to the specific requirements.

The various means of performing certain different functions certainly need not coexist only in the illustrated realisation, but may be per se present in many embodiments, also not illustrated.

FIG. 8 is shown as a flat sheet (102) divided into two sections (103) arranged opposite one another and present, each having a substantially triangular shape with concentric vertices, that define a flat central area (104) which may possibly be perforated, and first bases (105), curved to various extents.

The sections (103) are formed so that they can be folded by combining the respective first sides (106) adjacent that, once joined together by such sutures, define a containment structure for a breast implant.

In correspondence of the lower septum (103) projects, substantially in correspondence of its longitudinal central axis (115), an appendice (114) that has a shape substantially linear radiused to the third sides (118a, 118b) each having an end portion which substantially arched is connected to the first base (105) of the septum (103) bottom.

Corresponding with the vertex in which converge the first sides (106) of the two baffles (103) which are advantageously formed from the cut (122) shaped eyelet.

Although this solution allows the obtainment of a containment structure for a breast implant which, thanks to the presence of the appendix (114) allows a box-like structure to be attained, which is then interposed between the skin and the pectoralis major muscle and the pectoralis major muscle suture is stretched.

The characteristics indicated as advantageous, convenient or similar may also be omitted or be replaced with equivalents.

The invention claimed is:

1. Medical device (1), made of biomaterial, for implant-based breast reconstruction, having a flat original shape of plane geometry, with sections, which sutured together define the front part (9), lateral (10a, 10b), upper (11) and lower (12) of a box element (13), at least one of the sections (3, 103) having at least one appendix (14a, 14b, 114) adapted to define the rear part (19) of the box element (13), said box element (13) being adapted to wrap and containing integrally a breast prosthesis (8), said box element (13) being configured to be interposed between the subcutaneous layer and the pectoralis major muscle (21) and being suturable to the latter, wherein the flat sheet is cut so as to define three distinct septa, which each have a substantially triangular shape with concentric vertices, with a central zone, flat, possibly perforated, and with first bases slightly arched, said septa being formed in such way that they can be folded by combining the respective first sides adjoining so that, once sutured together, define a containment structure for a breast implant.

2. The device according to claim 1, wherein said partitions (3), once pushed together and sewn at the respective first sides (6) contiguous to, define the front part (9), lateral (10a, 10b), upper (11) and lower (12) of a box element (13).

3. The device according to claim 1 wherein at least one of said sections has two appendages (14a, 14b, protruding from said base (5), substantially equal to each other and are arranged approximately symmetrically to a longitudinal central axis (15) of said overlying septum (3).

4. The device according to claim 3 which is characterized by the fact that each of said appendages (14a, 14b) has a substantially triangular shape with a second side (16) linear, a second base (17) substantially linear and a third side (18) substantially arcuate.

5. The device according to claim 4, is characterized by the fact that, once said breast prosthesis (8) is inserted in correspondence of said containment structure (20) obtained by sewing said partitions (3), said appendages (14a, 14b) are folded and placed facing rearward of said partitions (3) and then said second sides (16), mutually adjacent, are sewn together by one or more sutures (7) as well as sewn to said first bases (5) in said appendices (14a, 14b).

6. The device according to claim 5 which is characterized by the fact that said appendages (14a, 14b) are to define the rear part (19) of said box element (13) that completely encloses the inside said breast prosthesis (8), said box element (13) being interposed between the skin and the pectoralis major muscle (21) and is then suturabile to the latter.

7. The device according to claim 1, characterized by the fact that it comprises a flat sheet (102) divided into two sections (103) arranged opposite one another and each having a substantially triangular shape with concentric vertices, said sections (103) defining a central (104) plane, possibly with perforations, and with first bases (105), variously curved.

8. The device according to claim 7, wherein said sections (103) are formed so that they can be folded by combining the respective first sides (106) adjacent so that, once joined together with stitches, define a containment structure for a breast implant.

9. The device according to claim 8 wherein, in correspondence with at least one of said sections (103) protrudes, substantially at the longitudinal central axis (115) of said septum (103), an appendix (114) which presents a substantially inverted T to define a second base (117) substantially linear radiused to third sides (118a, 118b) each having a substantially arcuate end portion which is connected to the first base (105) of said at least one septum (103).

10. The device according to claim 9, wherein, in correspondence with the vertex in which converge said first sides (106) of said two sections (103) are formed with cuts (122) shaped eyelets.

* * * * *